(12) United States Patent
Sa et al.

(10) Patent No.: US 7,315,608 B2
(45) Date of Patent: Jan. 1, 2008

(54) COMBINED PANORAMIC AND CT (COMPUTED TOMOGRAPHY)PHOTOGRAPHING APPARATUS

(75) Inventors: Yong-Jae Sa, Osan Si (KR); Jae-Yoon Park, Hwaseong Si (KR); Young-Gyun Jin, Suwon Si (KR); Tae-Woo Kim, Hwaseong Si (KR)

(73) Assignee: E-Woo Technology Co., Ltd, Yongin-Si (KR)

( * ) Notice: Subject to any disclaimer, the term of this patent is extended or adjusted under 35 U.S.C. 154(b) by 39 days.

(21) Appl. No.: 11/297,921

(22) Filed: Dec. 9, 2005

(65) Prior Publication Data

US 2007/0030952 A1 Feb. 8, 2007

(30) Foreign Application Priority Data

Aug. 8, 2005 (KR) ...................... 10-2005-0072186

(51) Int. Cl.
*A61B 6/14* (2006.01)
(52) U.S. Cl. ........................................ 378/38; 378/191
(58) Field of Classification Search .................. 378/38, 378/4–20, 167, 168, 178, 191, 196–197
See application file for complete search history.

(56) References Cited

U.S. PATENT DOCUMENTS

| | | | | |
|---|---|---|---|---|
| 5,848,123 | A * | 12/1998 | Strommer | 378/98.8 |
| 6,118,842 | A * | 9/2000 | Arai et al. | 378/39 |
| 2004/0190678 | A1* | 9/2004 | Rotondo et al. | 378/38 |
| 2004/0247069 | A1* | 12/2004 | Arai et al. | 378/4 |
| 2006/0256921 | A1* | 11/2006 | Tachibana et al. | 378/116 |

\* cited by examiner

*Primary Examiner*—Hoon Song
(74) *Attorney, Agent, or Firm*—John K. Park; Park Law Firm

(57) ABSTRACT

Disclosed herein is a combined panoramic and computed tomography photographing apparatus. The apparatus includes, an X-ray source part, an X-ray sensor part having a panoramic sensor and/or a CT sensor, a rotary arm for arranging the X-ray source part and the X-ray sensor part thereon in such a way as to be opposed to each other, a rotary arm supporting member, and rotary arm driving means, wherein the panoramic sensor and the CT sensor are dedicated sensors respectively for panoramic photographing and CT photographing. The apparatus can obtain a CT image and a panoramic image by one photographing apparatus, and allow a user to previously set the optimum enlargement ratio according to panoramic photographing or CT photographing.

12 Claims, 4 Drawing Sheets

COMBINED PANORAMIC AND CT (COMPUTED TOMOGRAPHY)PHOTOGRAPHING APPARATUS

TECHNICAL FIELD

The present invention relates to a combined panoramic and CT (Computed Tomography) photographing apparatus, more particularly, to a combined panoramic and computed tomography photographing apparatus, in which an X-ray sensor part includes dedicated sensor for panoramic photographing and CT photographing.

BACKGROUND ART

In the field of the medical diagnosis, conventionally, an X-ray CT (Computerized Tomography) imaging apparatus is a photographing apparatus in which an X-ray beam of a predetermined amount is transmitted to a patient's site to be imaged or photographed, the transmitted X-ray amount is measured by an X-ray sensor and the measured data is recorded in a memory, and an X-ray absorbing rate of each point of the captured bodily region of the patient is obtained by a computer and is reconstructed into an image. In the field of the dental diagnosis, an X-ray panoramic photographing apparatus is an apparatus for conducting tomography while rotating along a locus suitable for the form of a dental arch.

The conventional X-ray CT photographing apparatus can obtain only a CT image, and the conventional panoramic photographing apparatus can obtain only a photographic image. Therefore, recently, combined panoramic and computed tomography photographing apparatuses have been proposed.

U.S. Pat. No. 6,118,842 discloses an X-ray imaging apparatus which can conduct both the CT imaging and the panoramic imaging. The apparatus includes: an X-ray source for generating X-rays, an X-ray sensor for detecting X-rays having passed through an object, and supporting means for supporting the X-ray source and the X-ray sensor so that the X-ray source and the X-ray sensor are opposed to each other across an object; and mode switching means for switching between a CT mode and a panorama mode. To detect X-rays, only one X-ray sensor is used, and the X-ray sensor is an area sensor which is capable to detect a large area. The X-ray imaging apparatus can obtain the tomography image by converting the photographic mode into the panoramic mode after obtaining the CT image by selecting the CT mode.

However, the conventional imaging apparatus conducts the CT photographing and the panoramic photographing using only one sensor, and hence, needs an expensive sensor capable of carrying out the two photographing functions.

DISCLOSURE OF INVENTION

Technical Problem

Accordingly, it is an object of the present invention to provide a combined panoramic and computed tomography photographing apparatus, which can obtain a CT image and a panoramic image by using a dedicated CT sensor for CT photographing and a dedicated panoramic sensor for panoramic photographing, and which can allow a user to previously set the optimum enlargement ratio according to panoramic photographing or CT photographing.

Technical Solution

To achieve the above object, the present invention provides a combined panoramic and computed tomography photographing apparatus. The combined panoramic and computed tomography photographing apparatus includes: an X-ray source part for generating X-rays; an X-ray sensor part having a panoramic sensor and/or a CT sensor for detecting X-rays which are generated from the X-ray source part and pass through an object; a rotary arm for arranging the X-ray source part and the X-ray sensor part thereon in such a way as to be opposed to each other; a rotary arm supporting member for supporting the rotary arm; and rotary arm driving means interposed between the rotary arm and the rotary arm supporting member for driving the rotary arm, wherein the panoramic sensor and the CT sensor are dedicated sensors respectively for panoramic photographing and CT photographing.

Advantageous Effects

The combined panoramic and computed tomography photographing apparatus according to the present invention includes the X-ray sensor part having a dedicated CT sensor for CT photographing and a dedicated panoramic sensor for panoramic photographing, thereby obtaining a CT image and a panoramic image. Furthermore, the present invention can allow a user to previously set the optimum enlargement ratio according to panoramic photographing or CT photographying. Moreover, conventionally, only one expensive X-ray sensor for conducting both of the panoramic photographing and the CT photographing has been used. However, the present invention uses a dedicated X-ray sensor for panoramic photographing and a dedicated X-ray sensor for CT photographing, thereby reducing costs.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

Figure 1:
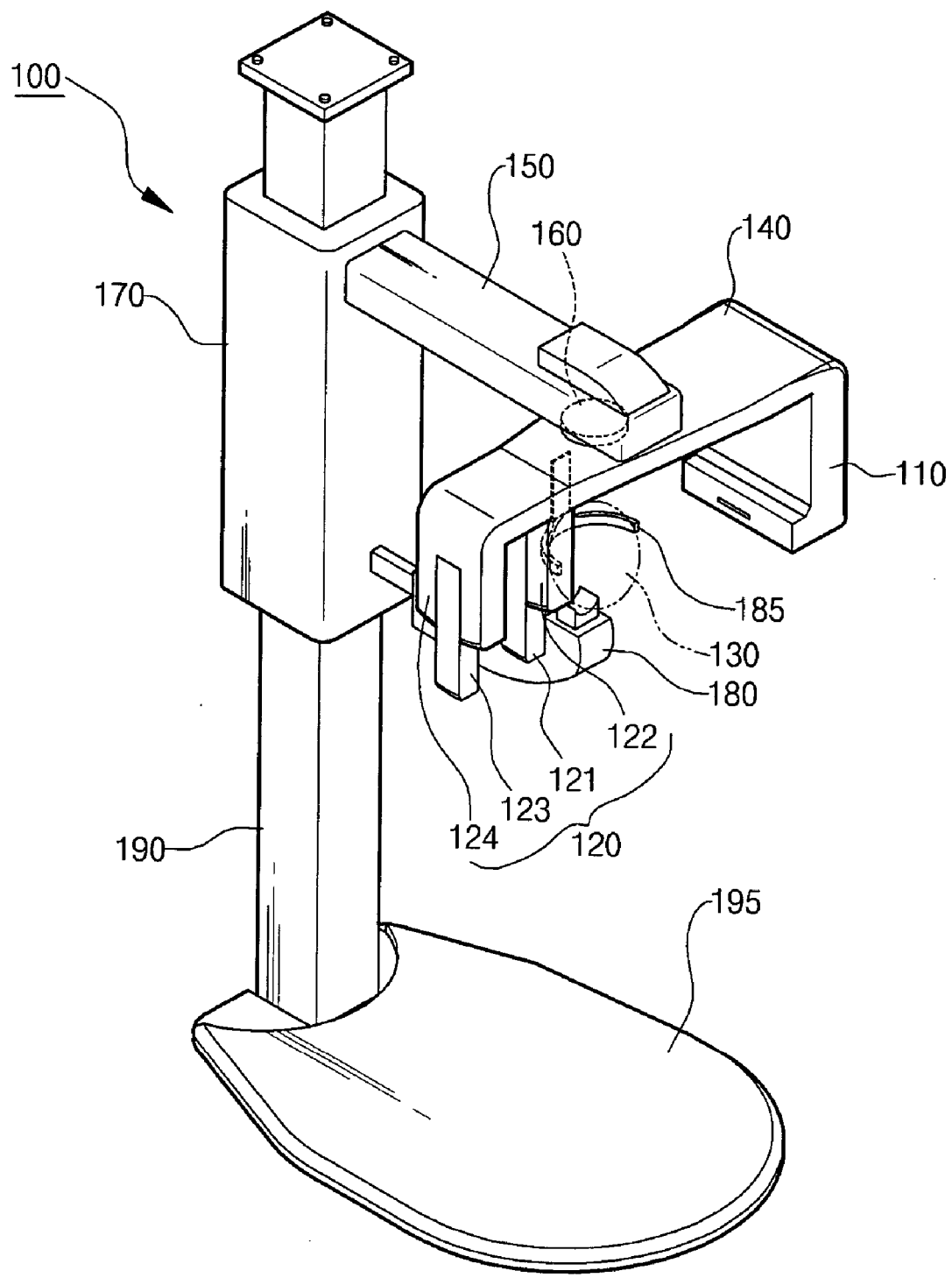
FIG. 1 is a perspective view of a combined panoramic and computed tomography photographing apparatus according to a first preferred embodiment of the present invention.

EXPLANATION ON ESSENTIAL REFERENCE NUMERALS IN DRAWINGS 100,200: combined panoramic and computed tomography photographing apparatus
110,210: X-ray source part
120,220: X-ray sensor part
121, 221: panoramic sensor 122, 222: first sensor mounting part
123, 223: CT sensor
124, 224: second sensor mounting part
140, 240: rotary arm
150: rotary arm supporting member
160: rotary arm driving means
170: elevation member
180: chin supporting member
185: head fixing means Best Mode Reference will now be made in detail to the preferred embodiments of the present invention, examples of which are illustrated in the accompanying drawings. The present invention is not restricted to the embodiments of the present invention but can be embodied in other various forms. The same reference numerals designate the same parts in the present invention.

Figure 2:
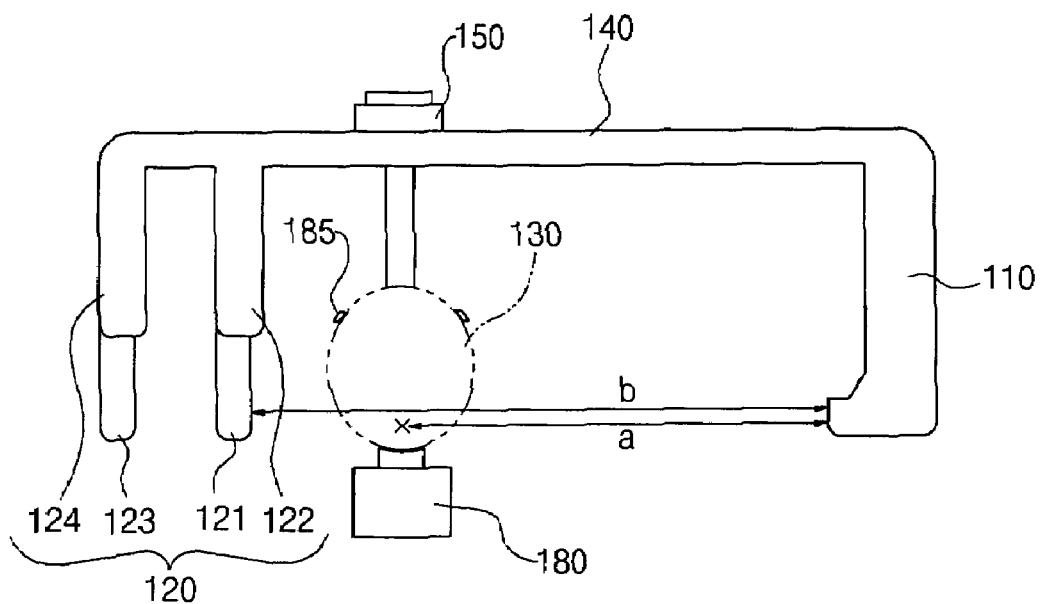
FIGS. 2 and 3 are front views for explaining photographing using the combined panoramic and computed tomography photographing apparatus according to the first preferred embodiment of the present invention.
Figure 3:
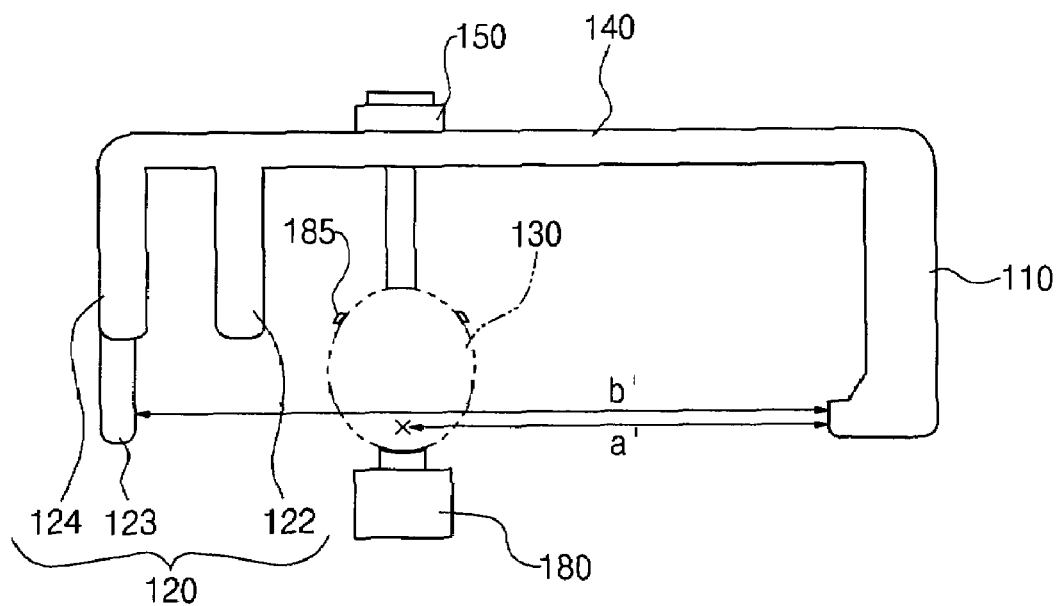

FIG. 1 is a perspective view of a combined panoramic and computed tomography photographing apparatus according to a first preferred embodiment of the present invention, and FIGS. 2 and 3 are front views for explaining photographing using the combined panoramic and computed tomography photographing apparatus according to the first preferred embodiment of the present invention.

Referring to FIG. 1, the combined panoramic and computed tomography photographing apparatus 100 includes a base 195, a supporting pole 190, an elevation member 170, a rotary arm supporting member 150, a rotary arm 140 on which an X-ray sensor part 120 and an X-ray source part 110 are opposed to each other, a chin supporting member 180, head fixing means 185, and rotary arm driving means 160, and can conduct CT photographing and panoramic photographing.

The base 195 supports the supporting pole 190 on which the above components are mounted, and the supporting pole 190 stands and is mounted at a side of the base 195.

The elevation member 170 is mounted on the supporting pole 190. The elevation member 170 includes a control motor for allowing a vertical displacement. Therefore, the apparatus 100 can regulate its own height according to a patient's height.

The chin supporting member 180 is mounted at the lower portion of the elevation member 170 in nearly orthogonal direction to the elevation member 170. The chin supporting member 180 is formed to position the patient's chin thereon. At this time, the patient's head is located between the X-ray sensor part 120 and the X-ray source part 110 disposed on the rotary arm 140. The chin supporting member 180 can be driven without regard to driving of the elevation member 170.

The rotary arm supporting member 150 is mounted at the upper portion of the elevation member 170 in nearly orthogonal direction to the elevation member 170. The rotary arm supporting member 150 supports the rotary arm 140 by the rotary arm driving means 160. The rotary arm supporting member 150 has lines (not shown) formed to allow movement of the rotary arm driving means 160, so that the rotary arm driving means 160 can move along the lines.

The rotary arm driving means 160 moves in a direction that the rotary arm supporting member 150 is connected to the elevation member 170 (X-axis movement), and in a horizontal direction which is orthogonal to the X-axis movement direction (X-axis movement). Furthermore, the rotary arm driving means 160 can be rotated on a central axis. That is, the rotary arm driving means 160 conducts the CT photographing or the panoramic photographing by driving the rotary arm 140. In case of the CT photographing, the rotary arm driving means 160 rotates the rotary arm 140 on the central axis in order to conduct photographing, and in case of the panoramic photographing, the rotary arm driving means 160 drives the rotary arm 140 on the X-axis and the Y-axis and drives the rotary arm 140 rotationally in order to conduct photographing. The rotary arm supporting member 150 and the elevation member 170 respectively include mechanical components, such as a control motor, therein which are necessary for driving of the rotary arm driving means 160.

In addition, The rotary arm supporting member 150 and the elevation member 170 further include a rotary arm driving means controller for controlling the rotary arm driving means 160 to move the rotary arm 140 along the fixed locus according to the CT photographing or the panoramic photographing. The mechanical function will not be described since it is clear to those skilled in the art.

The X-ray source part 110 is connected to an end of the rotary arm 140, and the X-ray sensor part 120 is connected to the other end of the rotary arm 140. The X-ray sensor part 120 and the X-ray source part 110 are opposed to each other.

The X-ray source part 110 emits and irradiates X-rays to a patient 130 or an object. The X-ray source part 110 includes an X-ray source and a collimator, so that the emitted X-rays pass through the object and are irradiated to the X-ray sensor part 120.

The X-ray sensor part 120 includes different dedicated CT sensors for the panoramic photographing and the CT photographing. The X-ray sensor part 120 further includes a first sensor mounting part 122 for mounting a panoramic sensor 121 and a second sensor mounting part 124 for mounting a CT sensor 123. the first sensor mounting part 122 is disposed at a portion which is near to the X-ray source part 110, and the second sensor mounting part 124 is disposed at a portion which is away from the X-ray source part 110 in order to regulate the enlargement ratio.

It would be appreciated that the first and second sensor mounting part 122 and 124 may have one of various shapes besides a slot form shown in the drawings.

The head fixing means 185 is located between the X-ray source part 110 and the X-ray sensor part 120. The head fixing means 185 is in the form of a hair band for surrounding the forehead part of the object (patient) 130, and fixes the head part of the patient. That is, the head fixing means 185 serves to fix the patient's head part together with the chin supporting member 180. Particularly, in case of the CT photographing, a clear image can be obtained without distortion when the patient's head part is not shaken, and so, the head fixing means 185 have an important role in the present invention. The head fixing means 185 is connected to a predetermined portion of the rotary arm supporting member 150 through the rotary arm 140 without being influenced by the driving of the rotary arm 140.

The head fixing means 185 includes means (not shown) for regulating its width according a size of the patient's head. Since people are different from one another in size of their head, the present invention can conduct photographing after regulating the width of a portion which surrounds the patient's forehead according to the size of the patient's head.

As described above, the first preferred embodiment of the present invention includes the X-ray sensor part 120 having all of the panoramic sensor 121 and the CT sensor 123. At this time, in the case where the CT photographing is conducted after the panoramic photographing, the user conducts the CT photographing after separating the panoramic sensor 121 from the first sensor mounting part 122.

Hereinafter, referring to FIGS. 2 and 3, a process to conduct the CT photographing or the panoramic photographing will be described.

Referring to FIGS. 2, the patient's head part which is the object 130 is located on the chin supporting member 180, and fixed by the head fixing means 185.

On the rotary arm 140 supported by the rotary arm supporting member 150, the X-ray source part 110 and the X-ray sensor part 120 are opposed to each other.

First, to conduct the panoramic photographing, the panoramic sensor 121 is mounted on the sensor mounting part 122 disposed on the X-ray sensor part 120. The panoramic sensor 121 may use a line scan sensor such as a single line scan sensor or a multi line scan sensor.

In case of the panoramic photographing, the user sets a rotation axis of the rotary arm 140 after setting the central axis (x) on a predetermined part of the patient's body, and then, rotates the rotary arm 140 along the circumference of the central axis and along the fixed locus of the rotation axis.

At this time, to obtain a clear image, it is preferable to conduct photographing after regulating the obtained image into the optimum enlargement ratio. The enlargement ratio means a ratio of the distance between the object 130 and the X-ray source part 110 to the distance between the X-ray sensor part 120 and the X-ray source part 110, and the obtained image is enlarged when the enlargement ratio is increased. When the enlargement ratio is too large, it is harmful to the patient since an amount of the generated X-rays is increased. On the contrary, when the enlargement ratio is too small, it is difficult to form a mechanical structure. Therefore, it is preferable to conduct photographing after selecting the optimum enlargement ratio in order to make the mechanical structure easy and obtain a good image.

In case of the panoramic photographing, it is preferable that the enlargement ratio is 1:1.1 to 1:1.6. Considering the mechanical aspect and an aspect of the highly clear image, it is the most preferable to conduct the panoramic photographing after setting the enlargement ratio to 1:1.3.

For instance, when a distance (a) between the object 130 and the X-ray source part 110 is 454 mm and a distance (b) between the X-ray sensor part 120 and the X-ray source part 110 is 590 mm, the enlargement ratio is about 1:1.3.

Referring to FIG. 3, after the panoramic photographing, the CT photographing is conducted. First, the panoramic sensor 121 is separated from the sensor mounting part 122.

The CT sensor may be an area sensor such as a single area sensor or a multi area sensor, or a sensor of a sequentially driving type.

The CT photographing is conducted by setting the central axis (X) at a predetermined position of the patient and rotating the rotary arm 140 on the central axis.

At this time, it is preferable that the enlargement ratio is 1:1.3 to 1:2. Particularly, it is preferable that the enlargement ratio is 1:1.6 when the patient's anterior teeth part is took by the CT photographing, but 1:1.5 when the patient's posterior teeth part is took by the CT photographing.

In the case where the patient's anterior teeth part is took by the CT photographing, if a distance (a") between the object 130 and the X-ray source part 110 is 424 mm and a distance (b") between the X-ray sensor part 120 and the X-ray source part 110 is 678, the enlargement ratio is about 1:1.6.

In the case where the patient's posterior teeth part is took by the CT photographing, if the distance (a") between the object 130 and the X-ray source part 110 is 424 mm and the distance (b") between the X-ray sensor part 120 and the X-ray source part 110 is 637 mm, the enlargement ratio is about 1:1.5.

To set the optimum enlargement ratio according to kinds of photographing, the distance among the object 130, the X-ray source part 110 and the X-ray sensor part 120 can be previously regulated. For instance, the X-ray sensor part 120 is manufactured to be attachable and detachable, and the first sensor mounting part 122 and the second sensor mounting part 124 are manufactured in such a way that a distance between the first sensor mounting part 122 and the second sensor mounting part 124 can be regulated. By the above structure, the user can previously set the optimum enlargement ratio according to the kinds of photographing before conducting photographing.

As described above, the combined panoramic and computed tomography photographing apparatus according to the first preferred embodiment of the present invention can conduct all of the CT photographing and the panoramic photographing, and conduct photographing after previously setting the optimum enlargement ratio according tow whether the panoramic photographing or the CT photographing is conducted.

Mode for Invention

Figure 4:
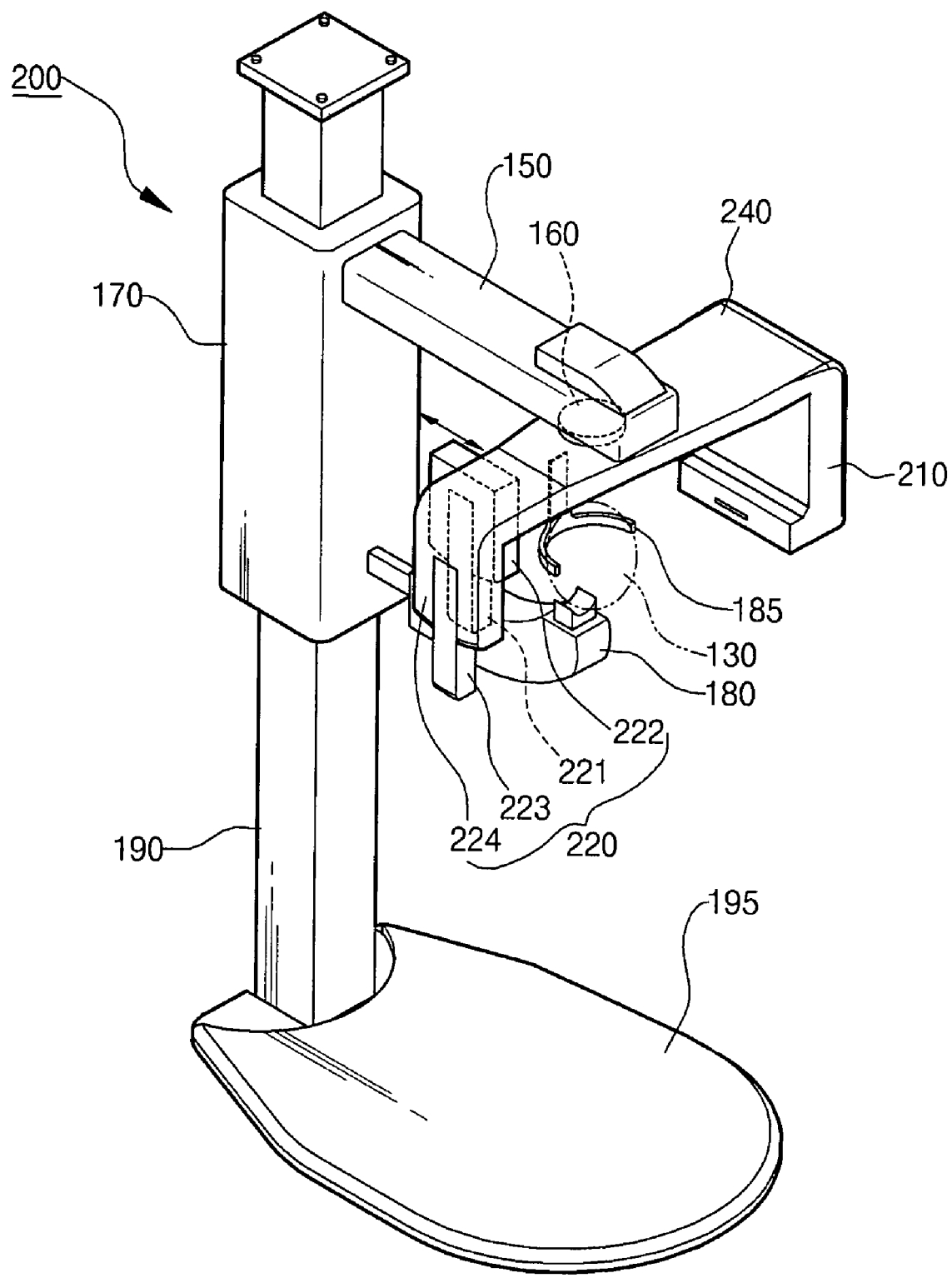
FIG. 4 is a perspective view of a combined panoramic and computed tomography photographing apparatus according to a second preferred embodiment of the present invention.
Figure 5:
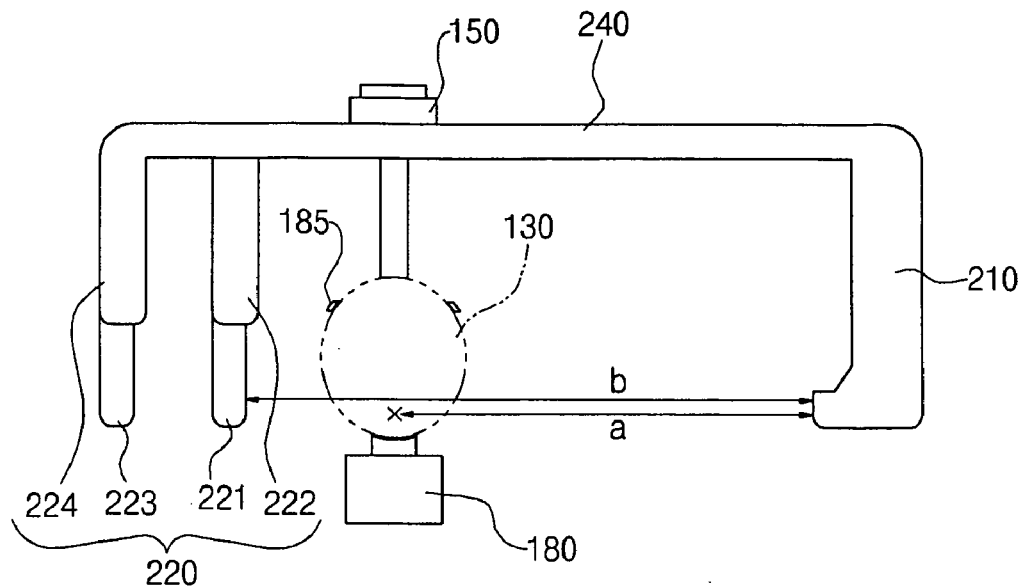
FIGS. 5 and 6 are front views for explaining photographing using the combined panoramic and computed tomography photographing apparatus according to the second preferred embodiment of the present invention.
Figure 6:
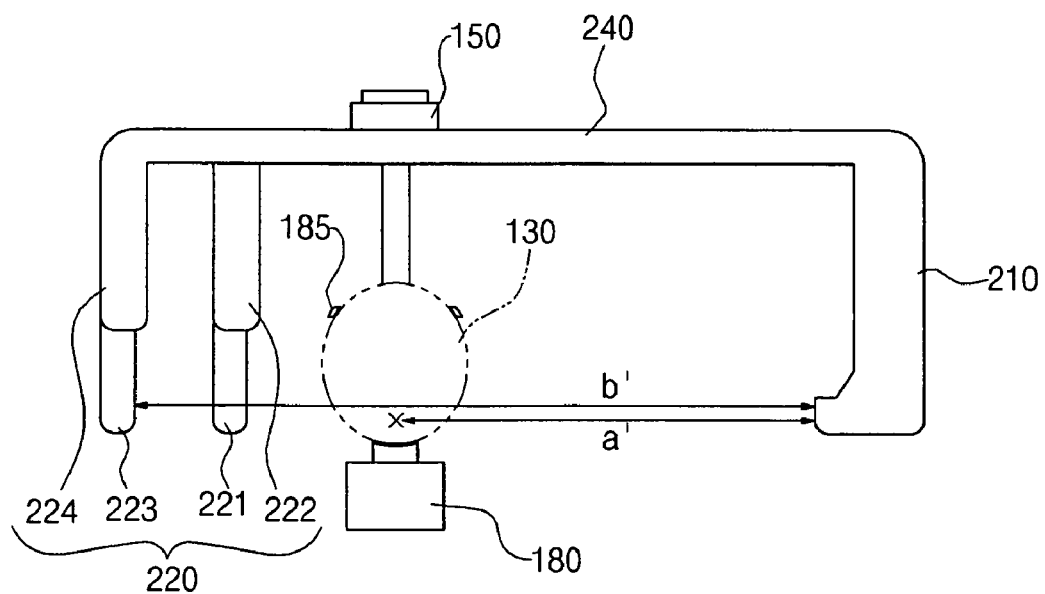

FIG. 4 is a perspective view of a combined panoramic and computed tomography photographing apparatus according to a second preferred embodiment of the present invention, and FIGS. 5 and 6 are front views for explaining photographing using the combined panoramic and computed tomography photographing apparatus according to the second preferred embodiment of the present invention.

Referring to FIG. 4, the combined panoramic and computed tomography photographing apparatus 200 includes a base 195, a supporting pole 190, an elevation member 170, a rotary arm supporting member 150, a rotary arm 240 on which an X-ray sensor part 220 and an X-ray source part 210 are opposed to each other, a chin supporting member 180, head fixing means 185, and rotary arm driving means 160, and can conduct CT photographing and panoramic photographing.

The X-ray source part 210 is connected to an end of the rotary arm 240, and the X-ray sensor part 220 is connected to the other end of the rotary arm 240. The X-ray sensor part 220 and the X-ray source part 210 are opposed to each other.

The X-ray source part 210 emits and irradiates X-rays to a patient 130 or an object. The X-ray source part 210 includes an X-ray source and a collimator, so that the emitted X-rays pass through the object and are irradiated to the X-ray sensor part 220.

The X-ray sensor part 220 includes a dedicated panoramic sensor 222 and a dedicated CT sensor 223 for the panoramic photographing and the CT photographing.

The X-ray sensor part 220 further includes a first sensor mounting part 222 for mounting a panoramic sensor 221 and a second sensor mounting part 224 for mounting a CT sensor 223. the first sensor mounting part 222 is disposed at a portion which is near to the X-ray source part 210, and the second sensor mounting part 224 is disposed at a portion which is away from the X-ray source part 210 in order to regulate the enlargement ratio.

It would be appreciated that the first and second sensor mounting part 222 and 224 may have one of various shapes besides a slot form shown in the drawings.

The second preferred embodiment according to the present invention includes the X-ray sensor part 220 having all of the panoramic sensor 221 and the CT sensor 223. At this time, to conduct the CT photographing after the panoramic photographing, the first sensor mounting part 22 on which the panoramic sensor 221 is mounted slides in a predetermined direction. That is, the first sensor mounting part 222 can be slid in a direction of the elevation member 170 (arrow direction in the drawing) or in an opposite direction so as not to detect X-rays generated from the X-ray source part 210.

The above is profitable when the first sensor mounting part 222 takes the slot form for fitting the panoramic sensor thereinto or a form that the panoramic sensor is mounted thereon.

Hereinafter, referring to FIGS. 5 and 6, a process to conduct the CT photographing or the panoramic photographing will be described.

Referring to FIG. 5, to conduct the panoramic photographing, the panoramic sensor 221 is mounted on the first sensor mounting part 222 disposed on the X-ray sensor part 220. The panoramic sensor 221 is a line scan sensor.

In case of the panoramic photographing, after a central axis (X) is set at a predetermined part of the patient's body, a rotation axis of the rotary arm 240 is set, and then, the rotary arm 140 is rotated along the circumference of the central axis and along the fixed locus of the rotation axis.

Referring to FIG. 6, the CT photographing is conducted after the panoramic photographing. At this time, differently from the first preferred embodiment, the panoramic sensor 221 is not separated from the first sensor mounting part 222, but the first sensor mounting part 222 on which the panoramic sensor 221 is mounted can be slid in a predetermined direction. That is, the first sensor mounting part 222 can be slid in the predetermined direction so that the panoramic sensor 221 does not detect X-rays generated from the X-ray source part 210.

At this time, the first sensor mounting part 222 can be automatically slid without regard to driving of the rotary arm 240, or manually slid in the predetermined direction.

In case of the CT photographing, after the central axis (X) is set at the predetermined part of the patient's body, the rotary arm 240 is rotated on the central axis.

INDUSTRIAL APPLICABILITY

The combined panoramic and CT photographing apparatus according to the present invention is usable in various fields such as a medical treatment, dental treatment, and so on. The combined panoramic and CT photographing apparatus can conduct both of the panoramic photographing and the CT photographing using the dedicated X-ray sensors for the panoramic photographing and the CT photographing.

The invention claimed is:

1. A combined panoramic and computed tomography photographing apparatus comprising:

an X-ray source part for generating X-rays;

an X-ray sensor part having a panoramic sensor and a CT sensor for detecting X-rays which are generated from the X-ray source part and pass through an object;

a rotary arm for arranging the X-ray source part and the X-ray sensor part thereon in such a way as to be opposed to each other;

a rotary arm supporting member for supporting the rotary arm; and rotary arm driving means interposed between the rotary arm and the rotary arm supporting member for driving the rotary arm;

wherein the X-ray sensor part includes a first sensor mounting part for mounting the panoramic sensor and a second sensor mounting part for mounting the CT sensor, and the panoramic sensor and the CT sensor are dedicated sensors respectively for panoramic photographing and CT photographing.

2. A combined panoramic and computed tomography photographing apparatus according to claim 1, wherein the first sensor mounting part is located near to the X-ray source part, but the second sensor mounting part is located away from the X-ray source part.

3. A combined panoramic and computed tomography photographing apparatus according to claim 2, wherein in case of a CT photographing, the panoramic sensor is separated from the first sensor mounting part so as not to detect X-rays generated from the X-ray source part.

4. A combined panoramic and computed tomography photographing apparatus according to claim 2, wherein in case of the CT photographing, the first sensor mounting part on which the panoramic sensor is mounted slides in a predetermined direction so as not to detect X-rays generated from the X-ray source part.

5. A combined panoramic and computed tomography photographing apparatus according to claim 1, wherein an enlargement ratio means a ratio of a distance between the object and the X-ray source part to a distance between the X-ray sensor part and the X-ray source part, and wherein in case of the CT photographing, the enlargement ratio is 1:1.3 to 1:2.

6. A combined panoramic and computed tomography photographing apparatus according to claim 5, wherein in case of the CT photographing, the enlargement ratio is 1:1.5 or 1:1.6.

7. A combined panoramic and computed tomography photographing apparatus according to claim 1, wherein an enlargement ratio means a ratio of a distance between the object and the X-ray source part to a distance between the X-ray sensor part and the X-ray source part, and wherein in case of the panoramic photographing, the enlargement ratio is 1:1.1 to 1:1.6.

8. A combined panoramic and computed tomography photographing apparatus according to claim 7, wherein in case of the panoramic photographing, the enlargement ratio is 1:1.3.

9. A combined panoramic and computed tomography photographing apparatus according to claim 1, wherein the panoramic sensor is a line scan sensor.

10. A combined panoramic and computed tomography photographing apparatus according to claim 1, wherein the CT sensor is an area sensor.

11. A combined panoramic and computed tomography photographing apparatus according to claim 1, further comprising a rotary arm driving means controller for controlling the rotary arm driving means to move the rotary arm along the fixed locus according to the CT photographing or the panoramic photographing.

12. A combined panoramic and computed tomography photographing apparatus according to claim 1, further comprising:
   a supporting pole standing on a base;
   an elevation member mounted on the supporting pole in such a way as to elevate and displace in a vertical direction;
   a chin supporting member connected to the lower portion of the elevation member; and
   head fixing means located between the X-ray source part and the X-ray sensor part, and connected to a predetermined portion of the rotary arm supporting member,
   wherein the rotary arm supporting member is connected to the upper portion of the elevation member.

* * * * *